US007665811B2

(12) United States Patent
Johanning

(10) Patent No.: US 7,665,811 B2
(45) Date of Patent: Feb. 23, 2010

(54) STATION FOR TRANSPORTING AND DISPENSING SUPPLIES

(76) Inventor: Jason M. Johanning, 3323 N. 161st Ter., Omaha, NE (US) 68116

(*) Notice: Subject to any disclaimer, the term of this patent is extended or adjusted under 35 U.S.C. 154(b) by 226 days.

(21) Appl. No.: 11/384,598

(22) Filed: Mar. 20, 2006

(65) Prior Publication Data

US 2007/0216267 A1 Sep. 20, 2007

(51) Int. Cl.
*A61B 19/02* (2006.01)

(52) U.S. Cl. .................... 312/209; 312/290; 312/321.5; 312/249.12

(58) Field of Classification Search ................................ 312/249.11–249.13, 293.2, 321.5, 209
See application file for complete search history.

(56) References Cited

U.S. PATENT DOCUMENTS

| | | | | |
|---|---|---|---|---|
| 2,632,684 | A * | 3/1953 | Anderson | 312/290 |
| 2,865,529 | A * | 12/1958 | Sprouse | 312/290 |
| 4,019,793 | A * | 4/1977 | Gerding | 312/209 |
| 4,114,965 | A * | 9/1978 | Oye et al. | 312/249.12 |
| 5,016,948 | A * | 5/1991 | Welch et al. | 312/249.12 |
| 5,269,599 | A * | 12/1993 | Moring | 312/290 |
| 5,673,983 | A * | 10/1997 | Carlson et al. | 312/249.11 |
| 5,702,115 | A * | 12/1997 | Pool | 312/249.12 |
| 5,836,661 | A * | 11/1998 | Oldorf | 312/290 |
| 6,378,963 | B1 * | 4/2002 | Relyea et al. | 312/218 |
| 6,663,202 | B2 * | 12/2003 | Spann | 312/249.12 |
| 7,275,796 | B2 * | 10/2007 | Bochner et al. | 312/249.11 |
| 2006/0008539 | A1 * | 1/2006 | Tomioka | 424/725 |

FOREIGN PATENT DOCUMENTS

| | | | |
|---|---|---|---|
| EP | 507343 | * 10/1992 | 312/249.11 |

OTHER PUBLICATIONS

Harloff Website, 1 page, available at http://www.harloff.com/healthcareCarts/E-SeriesCarts/E30-4Kframe.htm. (information shown was available prior to Mar. 20, 2005).

Armstrong Medical Industries Website, 2 pages, available at http://www.armstrongmedical.com/ami/item.cfm?sction=1 &sbsection=2 &category=82&itemid=1965. (information shown was available prior to Mar. 20, 2005).

(Continued)

*Primary Examiner*—Hanh V Tran
(74) *Attorney, Agent, or Firm*—Fitch, Even, Tabin & Flannery

(57) ABSTRACT

A station for transporting organized medical supplies and dispensing such supplies, the station having a plurality of configurations. In the dispensing configuration, the supplies located in the station can be easily accessed without the need to touch or otherwise manipulate the station. This touch-free access aids to prevent the transmission of pathogens. An upper panel with a number of compartments for medical supplies is connected to the station body to facilitate such touch-free access. The upper panel also supports a touch-free dispenser for hand sanitizer. The station can also be configured easily to a more compact configuration for transport. For example, the dispensing panel is moved from an upright dispensing position to a lowered horizontal position for transportation. Caster assemblies supporting the station enhance mobility for transportation.

18 Claims, 8 Drawing Sheets

OTHER PUBLICATIONS

Future Health Concepts Website, 3 pages, available at http://www.futurehealthconcepts.com/medical_carts.asp.(information shown was available prior to Mar. 20, 2005).

Avalo Medical Carts Website, 6 pages, available at http://allpharmacyjobs.com/avalo_medical_carts.htm. (information shown was available prior to Mar. 20, 2005).

Photograph of unknown cabinet 1 (information shown was available prior to Mar. 20, 2005).

Photograph of unknown cabinet 2 (information shown was available prior to Mar. 20, 2005).

Photograph of unknown cabinet 3 (information shown was available prior to Mar. 20, 2005).

Photograph of unknown cabinet 4 (information shown was available prior to Mar. 20, 2005).

Photograph of unknown cabinet 5 (information shown was available prior to Mar. 20, 2005).

Photograph of unknown cabinet 6 (information shown was available prior to Mar. 20, 2005).

Photograph of unknown cabinet 7 (information shown was available prior to Mar. 20, 2005).

Photograph of unknown cabinet 8 (information shown was available prior to Mar. 20, 2005).

Photograph of unknown cabinet 9 (information shown was available prior to Mar. 20, 2005).

Photograph of unknown cabinet 10 (information shown was available prior to Mar. 20, 2005).

Photograph of unknown cabinet 11 (information shown was available prior to Mar. 20, 2005).

Photograph of unknown cabinet 12 (information shown was available prior to Mar. 20, 2005).

Garner, Julia S. "Guideline for Isolation Precautions in Hospitals." Center for Disease Control. CDC. (Feb. 18, 1997).

AK Coatings, Introducing AgION Antimicrobial-Coated Steel for Medical Equipment, 2006.

* cited by examiner

STATION FOR TRANSPORTING AND DISPENSING SUPPLIES

FIELD OF THE INVENTION

The present invention relates to a station for transporting and dispensing supplies and, more particularly, to a station that easily transports the supplies in an organized fashion and dispenses supplies without having to touch the station.

BACKGROUND OF THE INVENTION

A hospital requires numerous protective measures to ensure the control of germs and bacteria. Healthcare professionals establish protocol to ensure a sanitary environment for patients and healthcare providers. Patient isolation is one such practice. This procedure can become time-consuming and cumbersome depending on the number of patients, frequency of visits, and whether or not the hospital's facilities easily accommodate the procedure.

Patient isolation practices are essential for controlling the spread of infections in hospitals. The Center for Disease Control and Prevention (CDC) and the Hospital Infection Control Practices Advisory Committee (HIPAC) developed and revised a "Guideline for Isolation Precautions in Hospitals" to promote up-to-date isolation practices in hospitals. In addition to CDC and HICPAC Guideline, the Occupational Safety and Health Administration (OSHA) has issued a rule mandating the use of specific protective wear to reduce the risk of exposure to certain pathogens.

The Guideline for isolation precautions, under the CDC, is designed to reduce the risk of pathogen transmission in hospitals between patients, healthcare workers, visitors, and environmental objects. Nosocomial infection transmission requires a source of infecting microorganisms, a susceptible host, and a means of transmitting the microorganism. Sources include patients, personnel, visitors, in varying stages of the disease from acute sufferers to chronic carriers, and contaminated inanimate objects, such as equipment, medications, and supplies. Patient factors such as age, underlying disease, treatments, irradiation, and interruptions in the first line of defense mechanisms affect susceptibility to infections. Transmission of microorganisms, under the Guideline is divided into several categories: contact, droplet, airborne, common vehicle, and vectorborne. Methods of a microorganism's transmission affect how the microorganism is isolated. However, hospital's use certain basic isolation requirements for all isolated patients regardless of transmission route.

According to the CDC Guideline, contact is the most frequent transmission means. Direct-contact transmission occurs between two body surfaces, a susceptible host and an infected or colonized person. Indirect-contact transmission occurs via a contaminated intermediate object, such as instruments, needles, dressings, or supply stations. Another source of indirect-contact transmission is hands that are not washed and gloves that were not changed between patients.

Two other important routes of transmission are droplet and airborne transmission. Droplet transmission occurs when the source coughs, sneezes, talks, and during some treatment procedures which suspend droplets in the air for a short distance. Such short distances differentiate the droplet transmission from airborne transmission that occurs when very small-evaporated droplets or dust particles remain suspended in the air for long period of time.

As mentioned, hospitals design isolation protocol to prevent the spread of microorganisms. Isolation creates a barrier to disrupt pathogen transmission between sources and hosts. Barriers created decrease the opportunity for the harmful bacteria or germs to spread from one patient to another or from a patient to a healthcare provider. While isolation measures often depend on a patient's infection and/or condition, there are certain universal measures used for all isolated patients and certain measures used for every patient where there is potential for contact with bodily fluids. Precautions include hand washing, gloving, and strategic patient placement. For activities that may result in contact with certain body fluids, precautions may include masks, respiratory protection, eye protection, face shields, gowns, protective apparel, and patient-care equipment articles.

While isolation precautions are essential to controlling the spread of infections and diseases, there are costs to isolation procedures. Certain isolation precautions require environmental modifications, specialized equipment and procedures that may make patient visits inconvenient and time-consuming. The hurdles imposed by isolation protocol, may negatively affect a patient's treatment.

Research suggests that patient isolation frustrates a healthcare worker's ability to examine patients because of the additional effort required to gown and glove. The additional prep time before a patient visit can cause problems if a patient requires prompt care. The isolation precautions can also become an obstruction to ordinary care received by the patient. Therefore, making isolation practices easy to implement is important.

As stated, the prep routine completed by healthcare providers before visiting patients can consume unnecessary time. Before visiting isolated patients, attending healthcare providers must sanitize their hands, put on gloves, a gown, or apron (if there will be substantial contact with the patient, or patient's environment) and possibly a mask. Other required protocol may follow, depending on the transmission route of the pathogens. Gloves must be changed between tasks and procedures on the same patient, if the healthcare provider touches material possibly containing a high concentration of microorganisms. After the patient visit, the physician, nurse, or other healthcare provider must remove gloves and gowns as promptly as possible and then sanitize his or her hands.

Location of the items used for isolation procedures is extremely important. These procedures become more time-consuming when the needed equipment and supplies are difficult to find or manipulate. Such equipment and supplies should remain conveniently located near the patient and systematically organized. Further, since patient placement is an important component of isolation protocol, the isolation supplies such as gloves, masks, eye protection, gowns, and other equipment should be easily movable with the patient.

Hospitals want to ensure that the transmissions of infection causing pathogens are controlled while not unnecessarily interfering with patient care. However, current isolation practices often interfere because they are frustrating, confusing, and time-consuming. This is a result of the disorganized manner in which isolation tools, equipment, and supplies are kept. Throughout many hospitals medical carts used for isolation procedures are cluttered, disorganized, and crowded with cups, boxes of gloves and gowns, three-ring binders, papers, medical instruments, such as stethoscopes, and lab coats. Other bare-boned shelves used for isolation procedures may house only a box of gloves and a few hospital gowns. Many times the gloves, gowns, masks, or other protective supplies are not stocked at the isolation area, and this is only discovered after the station has been searched for the required items in times of urgent need. Even if the required supplies can eventually be found amidst the clutter, the disorganization eats into precious time and frustrates healthcare workers.

The search for needed supplies not only frustrates the healthcare provider, but also frustrates the primary goal of isolation precautions, to stop transmission of pathogens. During the search for the required tools and supplies, a healthcare provider unnecessarily touches environmental surfaces and inanimate objects that have a risk of contamination, thereby increasing the opportunity for pathogen transmission. Thus, systematically organizing the supplies not only decreases the interference that isolation precautions cause, but by making the preparation routine touch-free, the primary goal of the procedure, to stop germ and bacteria transmission, is enhanced. Aseptic procedures are important in an environment where the risk of infection is high. Decreasing the unnecessary handling and manipulation of equipment and supplies will assist hospitals in providing a sanitary environment.

Accordingly, there is a need for an improved cart for organizing, standardizing, and centralizing the equipment and supplies required for isolation procedures.

DESCRIPTION OF THE PREFERRED EMBODIMENTS

Figure 1:
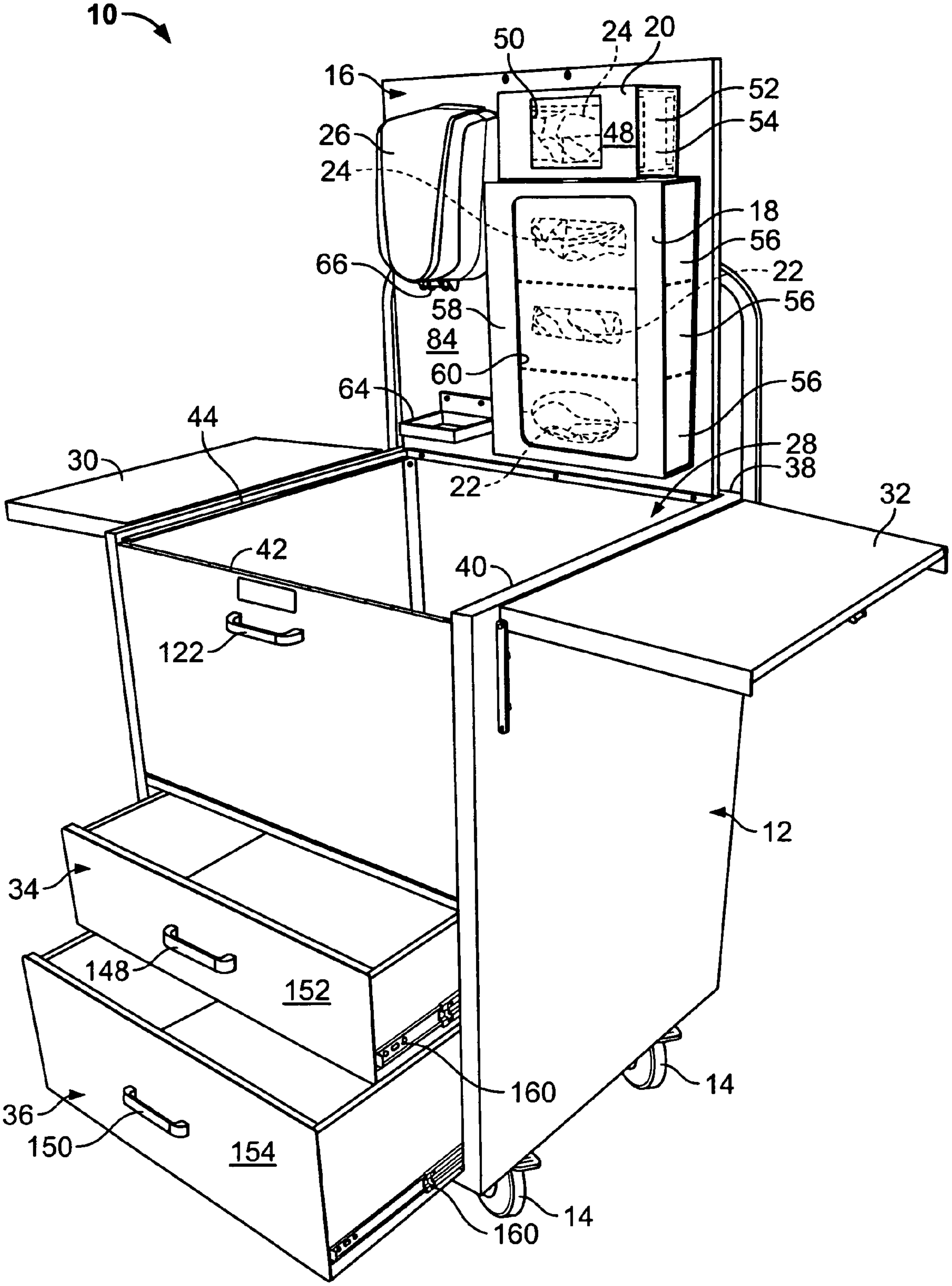
FIG. 1 is a front perspective view of a station having a panel and wings in an upright use position and a pair of bottom drawers that are shown in their open position.
Figure 2:
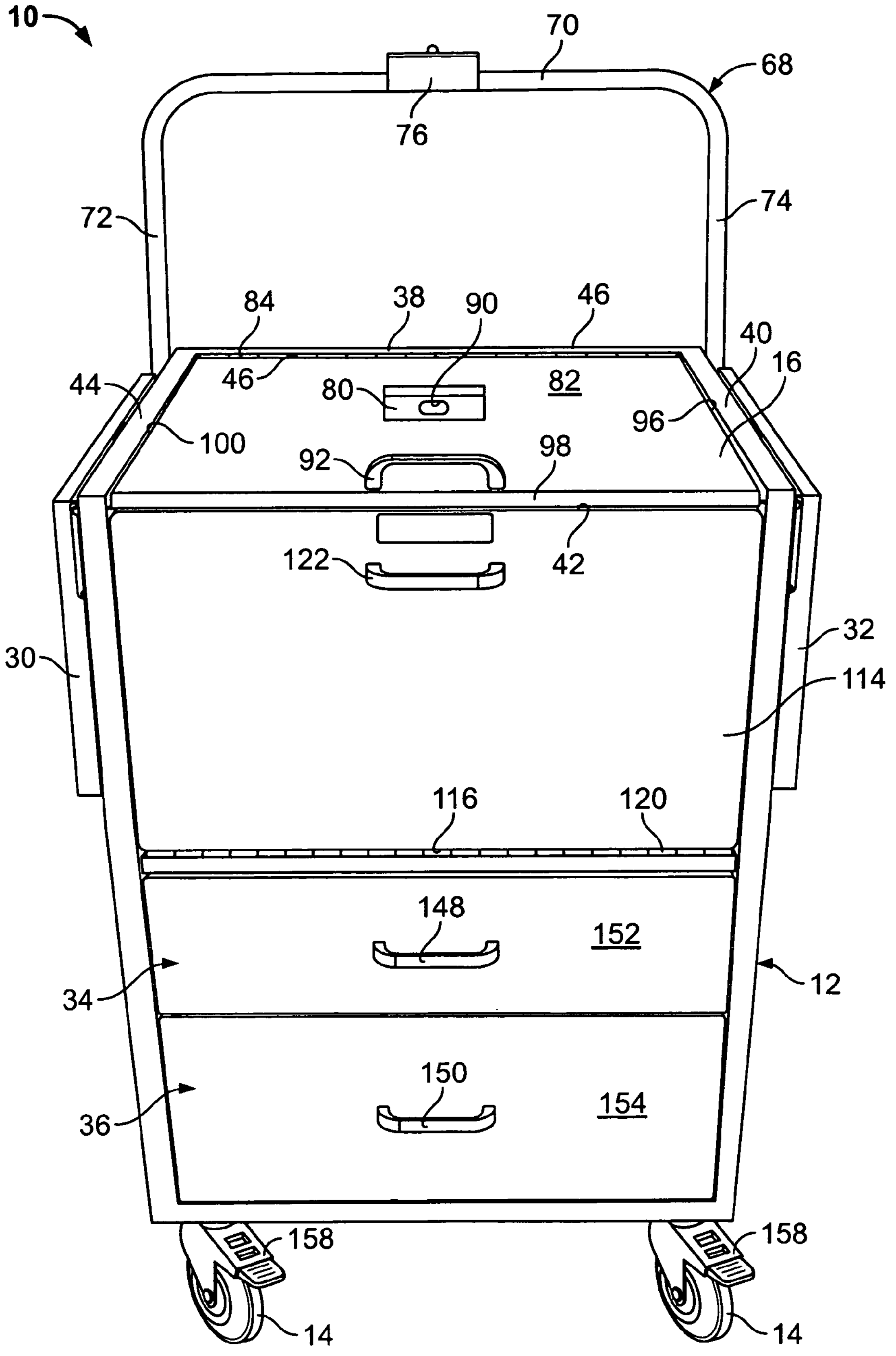
FIG. 2 is front perspective view of the station of FIG. 1 with the panel and wings in a down position and the drawers closed for enhanced mobility of the station.

With reference to FIG. 1, there is illustrated a station 10 for transporting organized medical supplies and dispensing such supplies. When the station 10 is configured to dispense medical supplies, as illustrated in FIG. 1, the supplies can be easily accessed without the need to touch the station 10. This touch-free access aids to prevent the spread of germs and bacteria. The station 10 also can be configured easily to a more compact configuration, as illustrated in FIG. 2, for transport.

More specifically, the station 10 includes a station body 12 supported on caster assemblies 14 for mobility. An upper panel 16 is attached to the upper portion of the body 12 and includes a number of compartments 18 and 20 to hold medical supplies, such as gloves 22 and masks 24, for touch-free dispensing, as discussed in further detail below. The panel 16 also supports a touch-free dispenser 26 for hand sanitizer. The panel 16 has an upright, dispensing position, as illustrated in FIG. 1, and a lowered, horizontal position for transportation, as illustrated in FIG. 2.

The body 12 also includes an open top bin 28 to store and dispense large medical supplies, such as gowns, in a touch-free manner when the panel 16 is located in its dispensing position. The body 12 further supports a pair of table wings 30 and 32 extending from opposite sides. As explained further below, the wings 30, 32 move from a use position (FIG. 1) to a compact storage and transport position (FIG. 2). Below the bin 28, the body includes a pair of drawers 34 and 36 to house medical supplies, such as those used to stock the upper compartments 18 and 20 when they become empty or other supplies not used as often.

Figure 6:
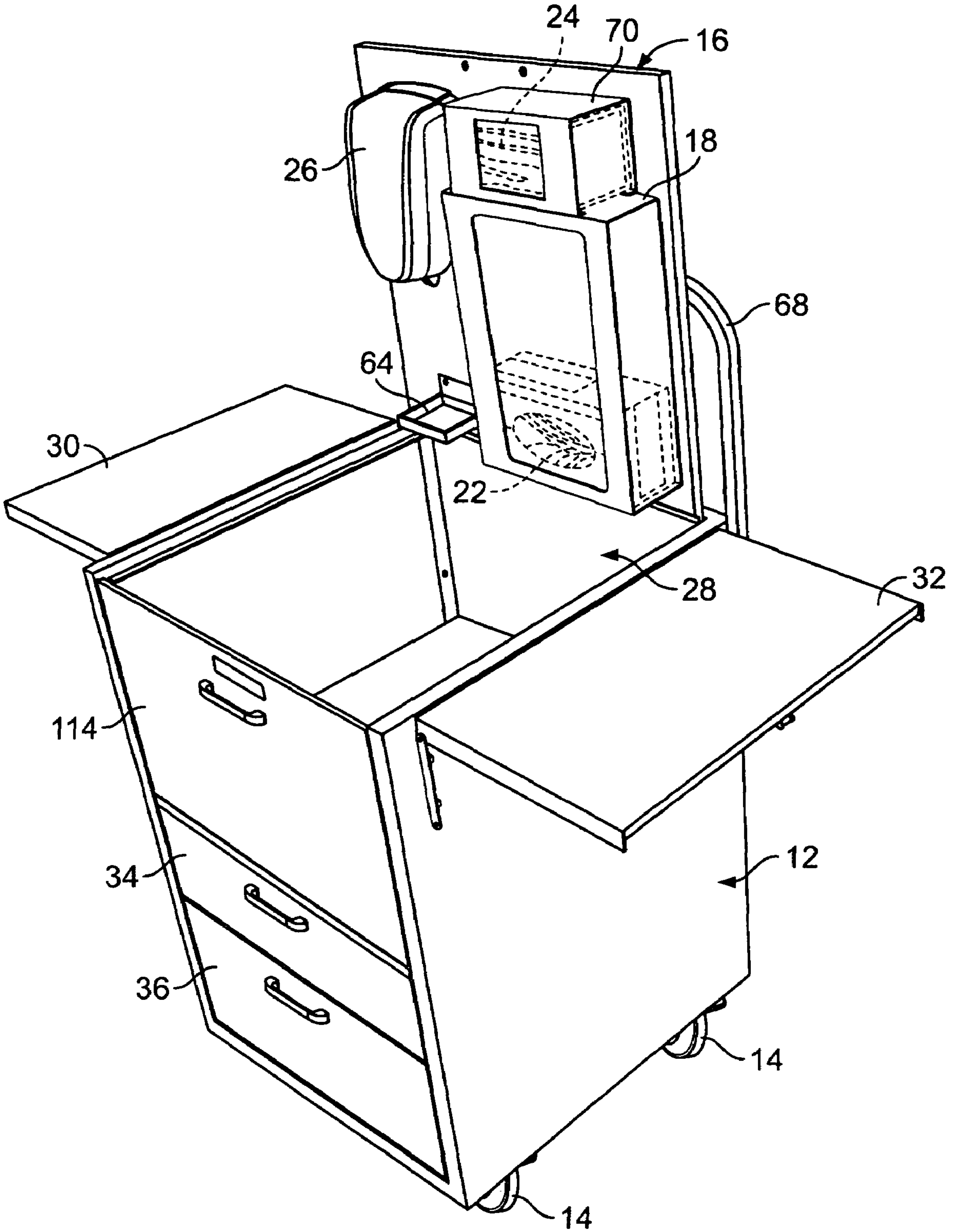
FIG. 6 is a front perspective view of the station of FIG. 1 having the panels and wings in the use position and the drawers and the bin door closed.
Figure 7:
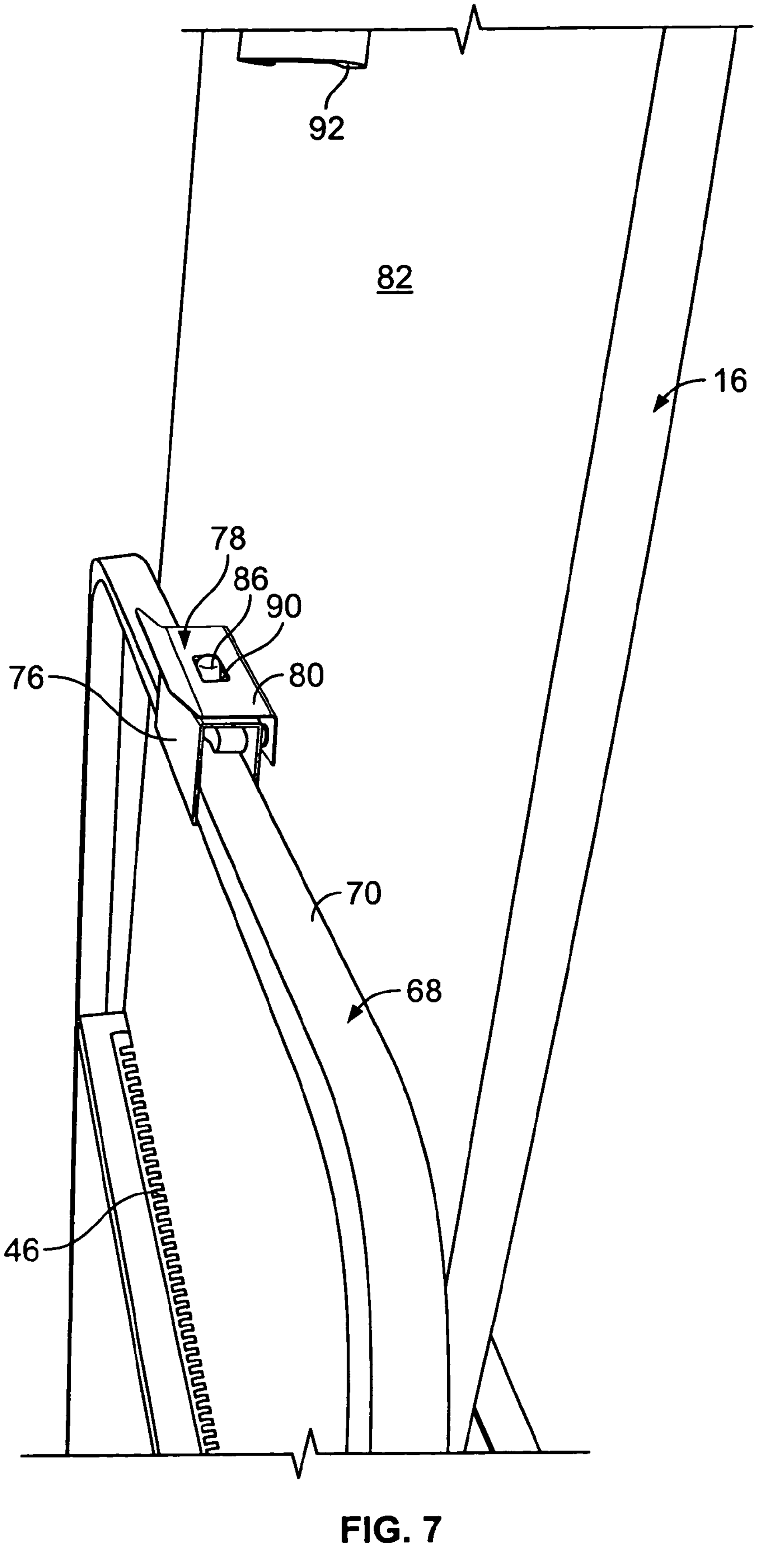
FIG. 7 is a rear perspective view of the station of FIG. 1 having the panel in the upright and locked position.

As illustrated in FIGS. 1, 6 and 7, the body 12 has four upper edges 38, 40, 42 and 44 that define the opening of the bin 28. The panel 16 is attached to the rear edge 38 of the body 12 station by hinge 46. The hinge 46 allows panel 16 to be positioned in the upright, dispensing position (FIG. 1) and pivoted downward to a lower, generally horizontal position (FIG. 2). In the lower position, the compartments 18, 20 and the dispenser 26 are recessed into the bin 28, and the bin 28 is covered. This compact configuration facilitates mobility of the station 10.

Each of the compartments 18 and 20 takes on preferably a rectangular sleeve like configuration. More specifically, the upper compartment 18 is preferably designed to dispense masks 24. The upper compartment 18 includes a front panel 48 defining a window 50 through which the masks 24 are dispensed. The upper compartment 18 also defines an open end 52 through which the box 54 of masks 24 can be inserted and the empty box can be removed.

The lower compartment 20 is located below the upper compartment 18 and is larger than the upper compartment 18. The lower compartment 20 preferably is designed to house three boxes 56 of different sized gloves 22. The lower compartment 20 includes a front panel 58 defining a window 60 through which the gloves 22 are dispensed. The lower compartment 20 also defines an open end 62 through which the box 56 of gloves 22 can be inserted and the empty box can be removed. Indeed, the preferred lower compartment 20 can hold multiple boxes in a stacked configuration so that more than one size of gloves (such as small, medium and large) can be dispensed through the same window 60. Both of the compartments 18 and 20 may be secured to the panel in any suitable manner, such as, for example, by glue, nuts and bolts, and rivets.

The dispensing panel 16 also supports a hand sanitizer dispenser 26 and a drip tray 64. The dispenser 26 preferably is located to the left and is of the type that automatically dispenses hand sanitizer upon placement of one's hands below the dispensing end 66. More specifically, the preferred dispenser 26 includes a sensor to initiate touch-free dispensing of sanitizer. The sensor recognizes when one's hands are below the dispensing end 66 and activates a motor in the dispenser to dispense sanitizer through the dispensing end 66 without hand contact. The preferred dispenser is a conventional dispenser that is commercially available.

The drip tray 64 extends out from the panel 16 to catch any drips of sanitizer from the dispenser 26 that do not land on one's hands so that the drips do not land in the bin 28. The dispenser 26 and the drip tray 64 may be attached to the panel 16 in any suitable manner, such as with glue, nut and bolts, or rivets. Also, the layout of the upper compartment 18, lower compartment 20, dispenser 26 and drip tray 64 may be different than the preferred layout discussed. For example, the compartments 18 and 20 may be on the left side of the panel 16 and the dispenser 26 and drip tray on the right side of the panel 16.

When the dispensing panel 16 is in the upright position, as in FIG. 1, the medical accessories are openly retrievable and available for use without requiring any manipulation of the station 20. For example, the medical accessories can include gloves 22 of various sizes and masks 24. The boxes typically dispense the gloves and masks in a similar fashion to the way tissues are commonly pulled from a box. Minimizing the amount of hand contact with the station and items stored therein minimizes the spread of germs and transfer of bacteria.

As shown in FIG. 2, a support bar 68 has an upper portion 70 and a pair of connecting arms 72 and 74 that connect the support bar 68 to a rear side 71 of the station body 12, adjacent to the rear edge 38 of the station body 12. The connecting arms 72, 74 may be mounted to the station body 12 utilizing attachment means such as rivets, or bolts, or may otherwise be incorporated into the station body 12 to secure the support bar 68. The upper portion 70 attaches a first component 76 of a locking mechanism 78 that is spring loaded. The first component 76 works in conjunction with a second component 80 of the locking mechanism 78 located on a backside 82 of the dispensing panel 16. The backside 82 of panel 16 is located opposite the dispensing side 84 of panel 16.

Figure 8:
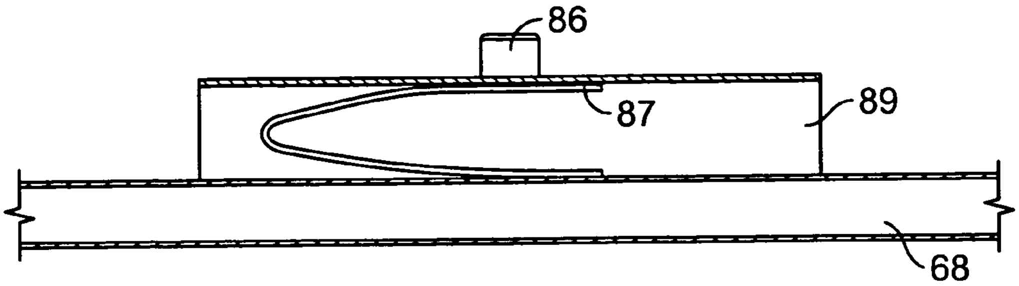
FIG. 8 is a cross-sectional view of a locking mechanism for the panel of the station of FIG. 1.

As illustrated in FIGS. 7 and 8, the locking mechanism 78 maintains the panel 16 in the upright position. The first component 76 is attached to the support bar 68 and includes a spring-loaded pin 86 that mates with the second component 80, which defines an opening 90 for the pin 86. The second component 80 is attached to the backside 82 of the panel 16. The spring-loaded pin 86 attaches to the compression spring 87 that is located within housing 89. The spring 87 biases the pin 86 away from the support bar 68 and toward the second component 80 of the locking mechanism 76, which is located on the backside 82 of the dispensing panel 16. As the panel 16 is being extended to the dispensing configuration, the second component 80 slides transversally over the first component 76 until the pin 86 snaps through the opening 90 of the second component 80, thereby locking the panel 16 into position. The second component 80 includes an upward angled front lip 91 that initially forces the pin 86 down against the bias of the spring 87. The pin 86 is pushed down out of the opening 90 when the panel 16 is to be lowered into the transport configuration.

The support bar 68 extends sufficiently high enough above the station body 12 to securely support the panel 16 when locked in the upright dispensing position as seen in FIGS. 1 and 7. For instances, the preferred support bar 68 has the upper portion 70 at least half way up the panel 16. When personnel retrieve gloves 22 or masks 24 by pulling these items from their respective compartments 18 and 20, the panel 16 will not undergo excessive movement due to the support bar 68 and the corresponding locking mechanism 78. The preferred support bar 68 has a square cross section, but it may have another shape such as a rectangular or circular cross-section.

The backside 82 of dispensing panel 16 further includes a handle 92. The handle 92 may be used to move the panel 16 from the lowered, horizontal position (FIG. 2) to the upright, dispensing position (FIG. 1). The dispensing panel 16 has four edges. When the panel 16 is in the lowered, horizontal position, a rear edge 94 corresponds to the rear edge 38 of bin 28, a right edge 96 corresponds to the right edge 40 of bin 28, a front edge 98 corresponds to the front edge 42 of bin 28, and a left edge 100 corresponds to the left edge 44 of bin 28. In the preferred embodiment, the handle 92 is nearest to the front edge 98 to facilitate easy lifting of the panel 16, attached to the station body 12 by hinge 46.

When dispensing panel 16 is located in the lowered, horizontal position, it rests on a pair of support guides 102 and 104. These support guides 102 and 104 may be two members attached to an inside of a left and right bin wall 106 and 108, may be formed extensions of the upper right and left edges 40 and 44 or may be recessed ledges formed into the station body 12. The support guides 102 and 104 are located below the right and left edges 40 and 44 so that when the panel 16 is in the lowered position, the backside 82 is generally flush with the edges 38, 40, and 44.

The left and right walls 106, 108 along with a rear inside wall 110, a bin door 114 and a floor 118 define the open top bin 28. The bin 28 may store large medical supplies, such as gowns. These gowns are accessible in a touch-free manner when the dispensing panel 16 is in the upright position. Further, the bin 28 is preferably located within arms reach of most adults eliminating the need to bend over to retrieve large medical supplies each time a new gown is required.

Figure 3:
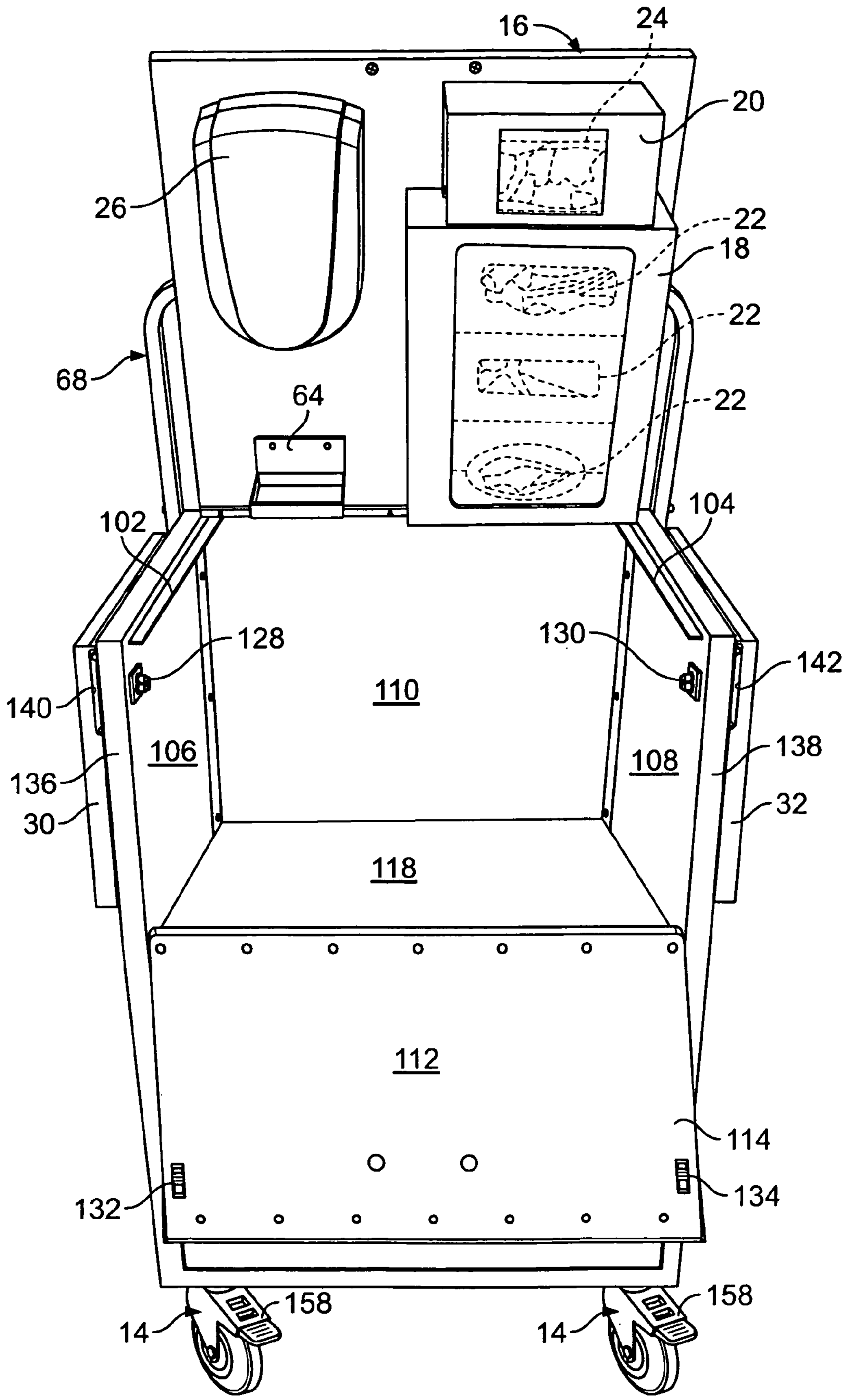
FIG. 3 is a front perspective view of the station of FIG. 1 having the panel in the use position and a front bin door open.

The bin door 114 includes a hinge 120 located on a bottom edge 116. Bin door 114 also incorporates a handle 122 and a pair of locking mechanisms to secure the bin door 114 in the closed position. In the preferred embodiment, the locking mechanisms are a pair of double roller catches. These double roller catches have a pair of first components 128 and 130 located on the left and right inner bin walls 106, 108 near the upper edges 40, 44. The first components 128, 130 mate with a pair of second components 132 and 134 located on the front inside bin wall 112, as seen in FIG. 3. When the bin handle 122 is pulled, the locking mechanism releases, and the bin door 114 may pivot down 180 degrees providing access to the items stored in bin 28.

Figure 4:
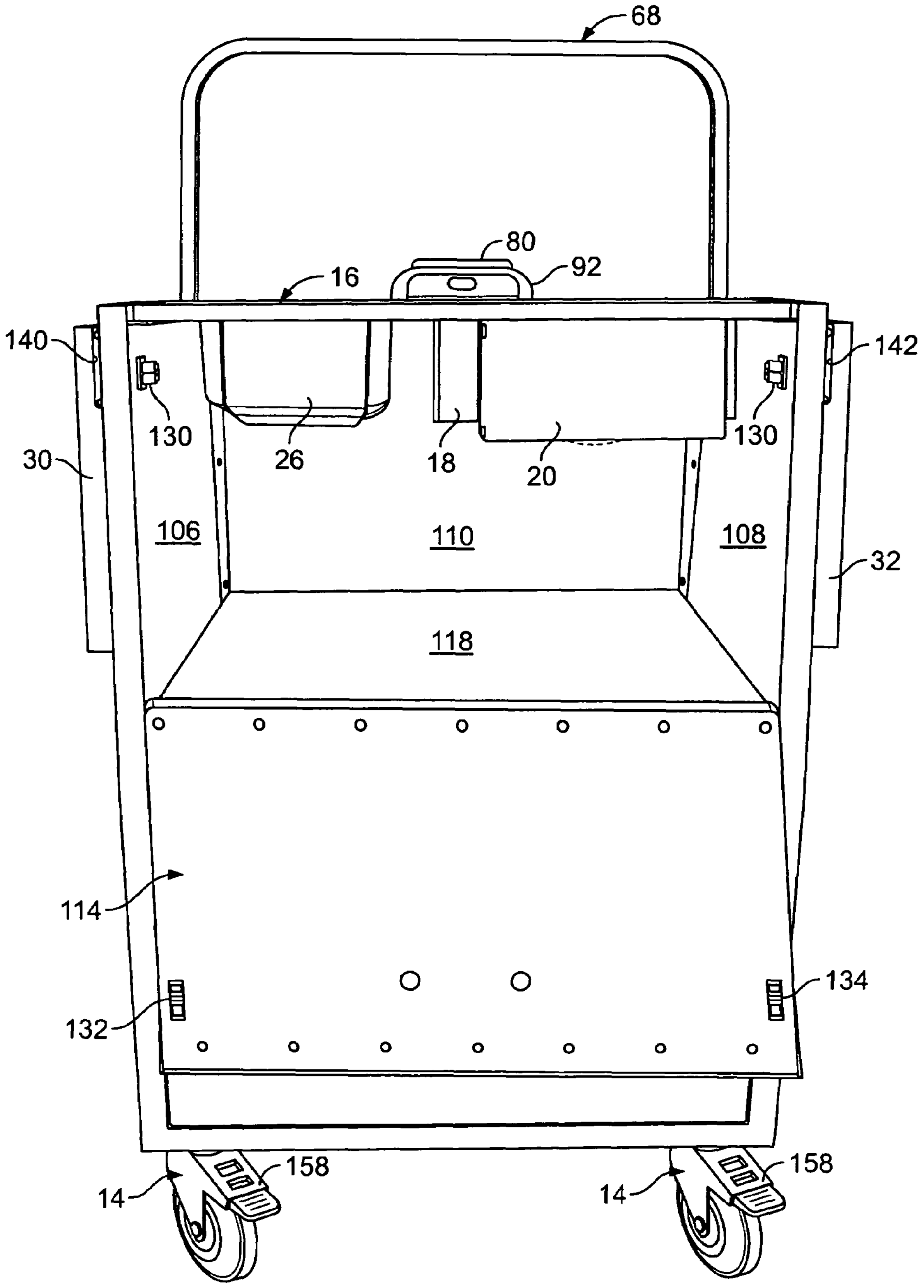
FIG. 4 is a front elevational view of the station of FIG. 1 having the panel and wings in the down position and the bin door open.

When the panel 16 is in the horizontal closed position (FIGS. 2 and 4) the compartments 18 and 12 and sanitizer dispensing 26 are positioned inside bin 28. As seen in FIG. 4, the bin door 114 can be opened while dispensing panel 16 is in the lowered position allowing for convenient access to the bin 28 even when panel 16 is in the lowered position.

Figure 5:
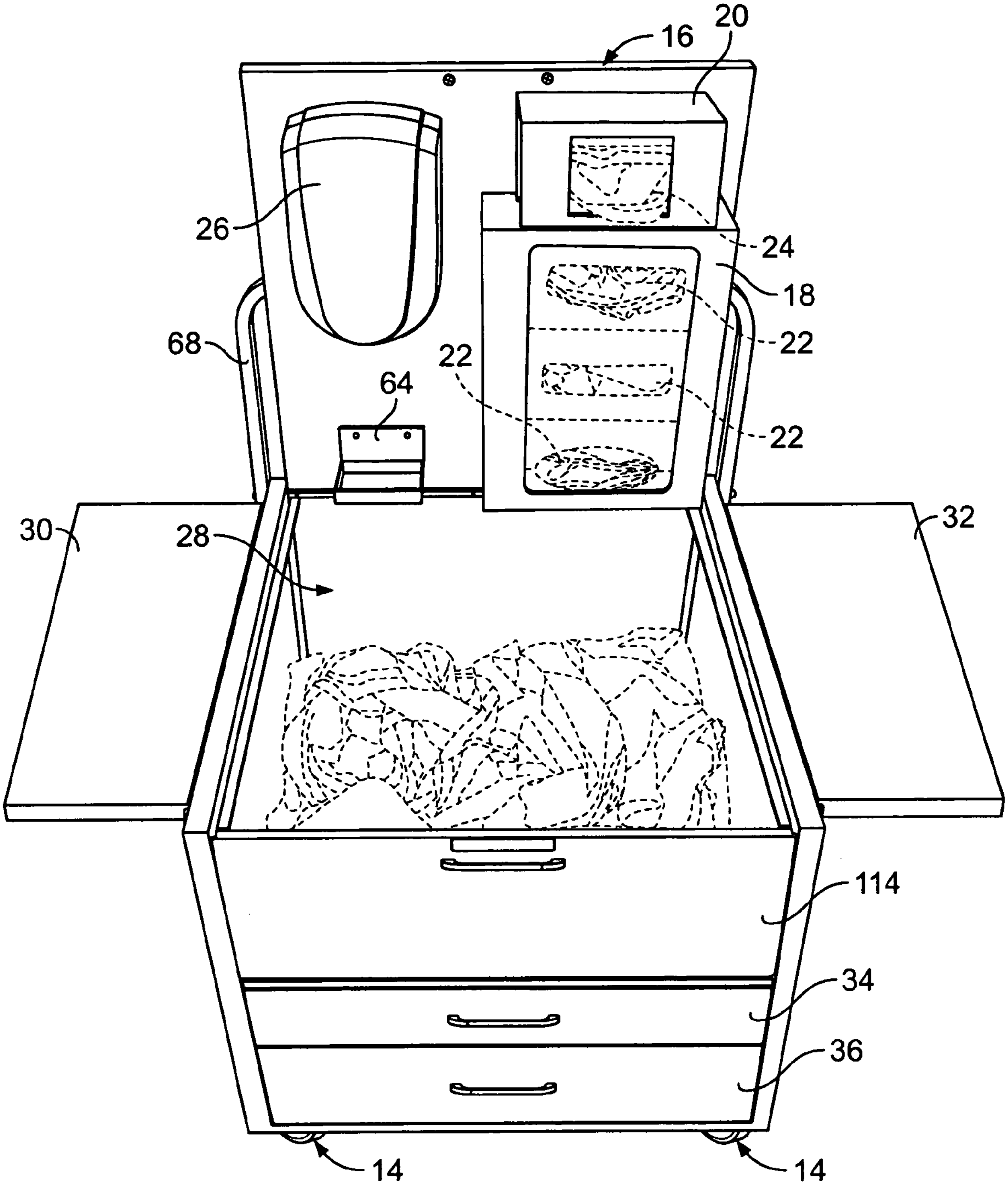
FIG. 5 is a front perspective view of the station of FIG. 1 having the panel and wings in the upright position and the drawers and the bin door closed.

In the preferred embodiment of FIGS. 1, 5, and 6, a pair of hinges 140 and 142 on each side of the body 12, attach each of the table wings 30 and 32 to a left and right side 136 and 138, respectively, of the station body 12. Each pair of hinges 140 and 142 includes one at the front of the body 12 and one at the rear of the body 12. The wings 30 and 32 may be supported in a horizontal use position by a locking mechanism 144. When in the use position, the wings 30 and 32 are flush with the side edges 40 and 44 of the station body 12 and remain supported from underneath by a brace or other support mechanism, allowing the wings 30 and 32 to be used as a flat work surface, such as for writing or supporting items. The wings 30 and 32 are collapsible to a compact transport configuration, as shown in FIG. 2. Therefore, the locking means 144 used underneath each of the wings 30 and 32 are preferably easily manipulated so that the wings 30 and 32 can be changed quickly from one configuration to another.

Figure 9:
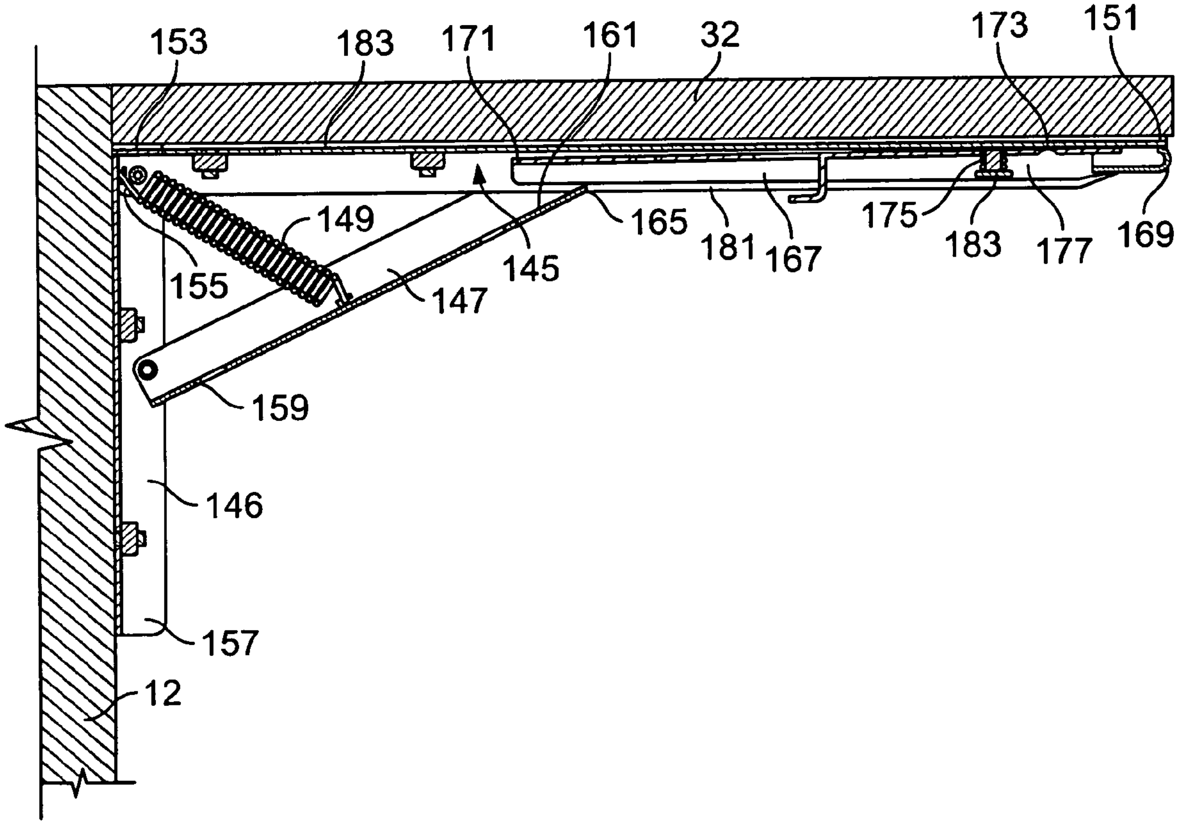
FIG. 9 is a cross-sectional view of a locking mechanism for the wing section of FIG. 1 were the wing is in the extended use position.

With reference to FIG. 9, the preferred locking mechanism 144 includes a wing support 145, a base support 146, a brace or strut 147, and a spring 149. The wing support 145 is attached to the underside of the wings 30 and 32 by nuts and bolts, or another suitable manner. The wing support 145 has a first end 151 that is located adjacent the outside edge of the wings 30 and 32. The second end 153 of wing support 145 is located adjacent to the station body 12. The base support 146 is attached to the station body 12 by nuts and bolts, or another suitable manner. The base support 146 has a first end 155 that is pivotally interconnected to the wing support 145 and a second end 157 located further down on the station body 12.

The brace 147 has a first end 159 that pivotally attaches to the base support 146 intermediate the ends 155 and 157. The brace support 147 has a second end 161 that is received in a notch 165 formed in the depending sides 181 on the wing support 145, when the locking mechanism 144 and the wings 30 and 32 are in the extended, use position. When the brace 147 interlocks with the notch 165, the brace 147 fastens into position and generally forms a triangle with the wing support 145 and the base support 146.

The depending sides 181 and the base 183 of the wing support 145 preferably form a U-shaped channel wherein a release member 167 is disposed therein. The release member 167 has a first end with a manually operated finger release 169 and a second end 171. The second end 171 is located adjacent to the wing support 145 and the second end 161 of the brace 147 when the wings 30 and 32 are in the extended position. To move the wings 30 and 32 from the extended position to the closed position, the finger release 169 is squeezed toward the base 183. The release member 167 acts as a lever by pivoting about an indentation 173 when the finger release 169 is engaged. The indentation 173 is located on the release member 167 between the finger release 169 and a spring 175. The compression spring 175 biases a portion 177 of the release member 167 between the indentation 173 and the second end 171 toward the wing support 145. A pin 185 supports the spring 173 against the base 183 of the wing support 145. Therefore, when the finger release 169 is moved toward the wing support 145, the release member 167 pivots causing the portion 173 of member 167 to push the brace 147 out of the notch 165. After the brace 147 is pushed out of the notch 165, the weight of the wing 30, 32 lowers the wings 30 and 32.

The spring 149 of the locking mechanism 144 has one end attached to the brace 147 intermediate its ends and the other end attached to the base support 146 near the end 155 that is pivotally connects the wing support 145 and the base support 146. The tension spring 149 pulls the locking mechanism 144 into the triangular configuration thereby extending the wing 30 and 32 into the use position. A catch 187 also may be added to guide and catch the moveable end 161 of the base 147 when the wing 30 and 32 is in the down position.

Below the bin 28 are the drawers 34 and 36 stacked one upon the other. Both of the drawers 34 and 36 include a drawer handle 148 and 150 centrally located on a front panel 152 and 154, respectively. Pulling the handles 148 and 150 causes the drawers 34 and 35 to slide along a pair of drawer slides or rails 160, thereby opening drawers 34 and 36 and displaying the contents which may include supplies for restocking the items displayed in panel 16 along with other equipment. Therefore, when the medical supplies on the dispensing panel 16 are depleted or running low, personnel may use the drawers to fulfill restocking requirements. Each of the drawers 34 and 36 can include a lock to limit access to the contents.

The caster assemblies 14 supporting the body 12 increase mobility of the station 10. The caster assemblies 14 also include a parking or locking mechanism 158 to prevent the station 10 from unintentional movement and ensure stability in between transport operations.

The surfaces of the station 10 also may include a silver ion antimicrobial steel coating. The coating is an antimicrobial agent that suppresses growth of bacteria and other microbes. The transmission of microorganisms in the hospital can be decreased if the surfaces of equipment incorporate such bacteria retardant properties.

While the invention has been described with respect to specific examples, including presently preferred modes of carrying out the invention, those skilled in the art will appreciate that there are numerous variations and permutations of the above-described apparatus that fall within the spirit and scope of the invention as set forth in the appended claims.

What is claimed is:

1. A station for transporting and dispensing medical supplies comprising:

portable station body;

a dispensing panel hingedly attached to an upper portion of the portable station body, the dispensing panel having a front side and a back side wherein the front side has a plurality of dispensing compartments secured thereto;

the portable station body and the dispensing panel having a transport configuration for enhanced mobility and a dispensing configuration for enhanced dispensing of medical supplies;

in the transport configuration, the dispensing panel is lowered to a position adjacent the portable station body to define a top of the portable station body such that the plurality of dispensing compartments are not readily accessible and, in the dispensing configuration, the dispensing panel is upright, extending from the portable station body in a generally vertical position wherein the plurality of dispensing compartments that are secured to the dispensing panel are directly accessible by a user in the dispensing configuration;

the portable station body having a panel support member to support the dispensing panel when the dispensing panel is in the generally vertical position and a locking mechanism having a first component provided on the panel support member and a second component provided on the back side of the dispensing panel to secure the dispensing panel in the generally vertical position; and wherein the plurality of dispensing compartments are arranged and employed to present medical supplies being openly retrievable and available for use without requiring any manipulation of the station other than direct contact with a retrieved medical supply once the portable station body and the dispensing panel are positioned in the dispensing configuration.

2. The station of claim 1 wherein the back side of the dispensing panel includes a handle secured thereto, the handle configured to permit the user to more easily move the dispensing panel from the transport configuration to the dispensing configuration.

3. The station of claim 2 wherein the panel support member is a bar attached to the portable station body and wherein the locking mechanism includes a first component mounted on the bar attached to the portable station body and a second component mounted on the dispensing panel and associated with the handle.

4. The station of claim 1 wherein the dispensing compartments comprise a dispensing device for dispensing sanitizer without requiring hand contact with the dispensing device.

5. The station of claim 4 wherein the dispensing device includes a sensor to automatically dispense sanitizer.

6. The station of claim 5 wherein the dispensing device is battery powered to automatically dispense sanitizer.

7. The station of claim 4 wherein the dispensing compartments comprise at least a first compartment having at least a first aperture through which to dispense medical supplies.

8. The station of claim 7 wherein the first compartment has at least a second aperture through which medical supplies are loaded into the first compartment.

9. The station of claim 8 wherein the dispensing compartments comprise a second compartment to dispense medical supplies.

10. The station of claim 2 wherein the portable station body defines a bin from which hospital supplies are openly retrievable once the portable station is in the dispensing configuration.

11. The station of claim 10 further comprises at least a first table extending from a first side of the body.

12. The station of claim 11 wherein the first table is hinged to the first side of the body and shifts between an extended use position and a downward transport position.

13. The station of claim 12 wherein the first table further includes a support located underneath the table to secure the table in the use position.

14. The station of claim 13 further comprises a second table extending from a second side of the portable station body, the second table being hinged to the second side of the portable station body and shifts between an extended use position and a downward transport position, and the second table having a support located underneath the table to secure the table in the use position.

15. The station of claim 10 further comprising at least a first drawer for storing medical supplies and equipment, the first drawer positioned below the bin.

16. The station of claim 7 wherein at least a portion of the station is coated with an antimicrobial substance.

17. The station of claim 16 wherein the antimicrobial substance is an antimicrobial silver ion substance.

18. The station of claim 10, wherein the dispensing panel in the lowered, transport configuration provides a lid to the bin.

* * * * *

UNITED STATES PATENT AND TRADEMARK OFFICE

CERTIFICATE OF CORRECTION

PATENT NO. : 7,665,811 B2
APPLICATION NO. : 11/384598
DATED : February 23, 2010
INVENTOR(S) : Jason M. Johanning It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 393 days.

Signed and Sealed this

Seventh Day of December, 2010

David J. Kappos
*Director of the United States Patent and Trademark Office*